United States Patent
Yamakage

(10) Patent No.: US 10,551,181 B2
(45) Date of Patent: Feb. 4, 2020

(54) BOARD INSPECTION MACHINE

(71) Applicant: FUJI CORPORATION, Chiryu-shi (JP)

(72) Inventor: Yusuke Yamakage, Chiryu (JP)

(73) Assignee: FUJI CORPORATION, Chiryu-shi (JP)

(*) Notice: Subject to any disclaimer, the term of this patent is extended or adjusted under 35 U.S.C. 154(b) by 0 days.

(21) Appl. No.: 15/735,419

(22) PCT Filed: Jun. 24, 2015

(86) PCT No.: PCT/JP2015/068274
§ 371 (c)(1),
(2) Date: Dec. 11, 2017

(87) PCT Pub. No.: WO2016/208019
PCT Pub. Date: Dec. 29, 2016

(65) Prior Publication Data
US 2018/0135976 A1 May 17, 2018

(51) Int. Cl.
*G01B 11/30* (2006.01)
*G01N 21/95* (2006.01)
(Continued)

(52) U.S. Cl.
CPC ............. *G01B 11/30* (2013.01); *G01N 21/01* (2013.01); *G01N 21/95* (2013.01); *H05K 13/08* (2013.01)

(58) Field of Classification Search
CPC ................. H05K 3/1216; H05K 13/08; Y10T 29/49133; Y10T 29/49121;
(Continued)

(56) References Cited

U.S. PATENT DOCUMENTS 4,615,093 A * 10/1986 Tews ............... H01L 21/681
29/407.04
4,959,898 A * 10/1990 Landman ........... H05K 13/0818
29/705
(Continued)

FOREIGN PATENT DOCUMENTS

JP 63-260129 A 10/1988
JP 2000-196300 A 7/2000
(Continued)

OTHER PUBLICATIONS

International Search Report dated Sep. 29, 2015, in PCT/JP2015/068274, filed Jun. 24, 2015.

*Primary Examiner* — Sang H Nguyen
(74) *Attorney, Agent, or Firm* — Oblon, McClelland, Maier & Neustadt, L.L.P.

(57) ABSTRACT

A board inspection machine includes a carrier conveyance device that loads, positions, and unloads a carrier member on which multiple individual boards are placed, solder paste being printed and a component being mounted on the individual boards; a board lifting-up device that lifts up the individual board, and a flatness inspection device that inspects flatness of the lifted individual board and determines usability of the individual board. As the multiple individual boards are sequentially lifted by the board lifting-up device and the flatness can be sequentially inspected by the flatness inspection device, efficient inspection may be performed. In addition, since full inspection is performed with respect to the flatness of the multiple individual boards, quality of the individual board may be improved.

9 Claims, 7 Drawing Sheets

(51) Int. Cl.
*H05K 13/08* (2006.01)
*G01N 21/01* (2006.01)

(58) Field of Classification Search
CPC ......... Y10T 29/49462; Y10T 29/53543; Y10T 29/4913; G06T 7/136; G06T 5/009; G06T 2207/30141; G01B 11/30; G01N 21/956; G01N 21/95; G01N 21/01
See application file for complete search history.

(56) References Cited

U.S. PATENT DOCUMENTS

| | | | | |
|---|---|---|---|---|
| 5,315,409 | A * | 5/1994 | Matsumura | G06K 9/38 358/448 |
| 5,379,514 | A * | 1/1995 | Okuda | H05K 13/0882 29/833 |
| 5,561,696 | A * | 10/1996 | Adams | G01N 23/043 378/58 |
| 5,628,110 | A * | 5/1997 | Sakaguchi | H05K 13/0413 29/840 |
| 5,778,525 | A * | 7/1998 | Hata | H05K 13/0413 29/714 |
| 5,836,504 | A * | 11/1998 | Koike | B23K 31/12 228/103 |
| 5,991,435 | A * | 11/1999 | Tsujikawa | G06T 7/0006 348/126 |
| 6,118,538 | A * | 9/2000 | Haugan | H05K 13/0812 356/623 |
| 6,178,626 | B1 * | 1/2001 | Hada | H05K 13/0812 29/833 |
| 6,246,789 | B1 * | 6/2001 | Hosotani | H05K 13/08 382/151 |
| 6,526,651 | B1 * | 3/2003 | Hwang | H05K 13/0061 29/740 |
| 6,606,788 | B1 * | 8/2003 | Morimoto | H05K 13/08 29/823 |
| 6,727,713 | B1 * | 4/2004 | Choi | G01N 21/8806 356/237.5 |
| 9,241,436 | B2 * | 1/2016 | Minamide | H04N 7/18 |
| 2002/0071601 | A1 * | 6/2002 | Kawada | H05K 13/0812 382/145 |
| 2012/0031952 | A1 * | 2/2012 | Hattori | H05K 3/1216 228/9 |
| 2012/0151756 | A1 * | 6/2012 | Amano | H05K 13/0413 29/720 |
| 2016/0037693 | A1 * | 2/2016 | Kurashina | H05K 13/08 29/739 |

FOREIGN PATENT DOCUMENTS

| | | |
|---|---|---|
| JP | 2001-60800 A | 3/2001 |
| JP | 2002-185103 A | 6/2002 |
| JP | 2010-261081 A | 11/2010 |
| JP | 2014-225500 A | 12/2014 |

* cited by examiner

BOARD INSPECTION MACHINE

TECHNICAL FIELD

The present disclosure relates to a board inspection machine for inspecting flatness of multiple individual boards placed on a carrier member.

BACKGROUND ART

As equipment for producing a board on which a large number of components are mounted, there are a solder printing machine, a component mounting machine, a reflow machine, a board inspection machine, and the like. It is common to connect this equipment in a row to construct a board production line. Among them, the component mounting machine includes a component transfer device that picks up a component from a component supply device and mounts it on the board loaded in a board conveyance device. Furthermore, there is also the component mounting machine including a coplanarity inspection device for checking a state of terminals of the component. According to this, lead curve of a leaded component, missing bumps or bump defects of a bump component, and the like are detected. One technical example relating to this type of the coplanarity inspection device is disclosed in PTL 1.

In an electronic component mounting method of PTL 1, two-dimensional data for positioning is obtained by imaging an electronic component, height data is obtained by imaging an electronic component on which angle correction is performed based on two-dimensional data, and three-dimensional data is finally obtained. According to this, in addition to lead floating inspection, since flatness inspection of electronic components having ball shaped terminals such as BGA and CSP can be performed at high speed and reliably, and a mounting takt time can be remarkably shortened.

CITATION LIST

Patent Literature

PTL 1: JP-A-2001-60800

SUMMARY

However, in accordance with miniaturization of terminals (leads, bumps) accompanying recent miniaturization of components, quality improvement relating to a mounting operation of the components further becomes necessary. That is, in PTL 1, flatness of a terminal of an electronic component is inspected. However, this is insufficient, and it is necessary to inspect the flatness of a board side on which the components are mounted. On the other hand, along with miniaturization of boards such as mobile phones, production forms of the boards have diversified. That is, in addition to a general production form in which boards are loaded and unloaded one by one and components are sequentially mounted, a production method in which a multiple board in which multiple small boards are integrated is separated after mounting components and a production method in which a mounting operation is performed in a state where multiple small boards are placed on a carrier member are also increasing. This type of small board is referred to as an individual board or a module board.

The present disclosure has been made in view of the problems of the above background art, and an object of the present disclosure is to provide a board inspection machine which can improve quality of individual boards by efficiently inspecting flatness of multiple individual boards placed on a carrier member.

The board inspection machine of the present disclosure for solving the problems includes a carrier conveyance device that loads, positions, and unloads a carrier member on which multiple individual boards are placed, solder paste being printed and a component being mounted on the individual board, a board lifting-up device that lifts up the individual board, and a flatness inspection device that inspects flatness of the lifted individual board and determines usability of the individual board.

According to the board inspection machine of the present disclosure, since the multiple individual boards are sequentially lifted by the board lifting-up device and the flatness can be sequentially inspected by the flatness inspection device, efficient inspection is performed. In addition, since full inspection is performed with respect to the flatness of the multiple individual boards, quality of the individual board is improved.

DESCRIPTION OF EMBODIMENTS (1. Configuration of Board Inspection Machine 1 of First Embodiment)

Figure 1:
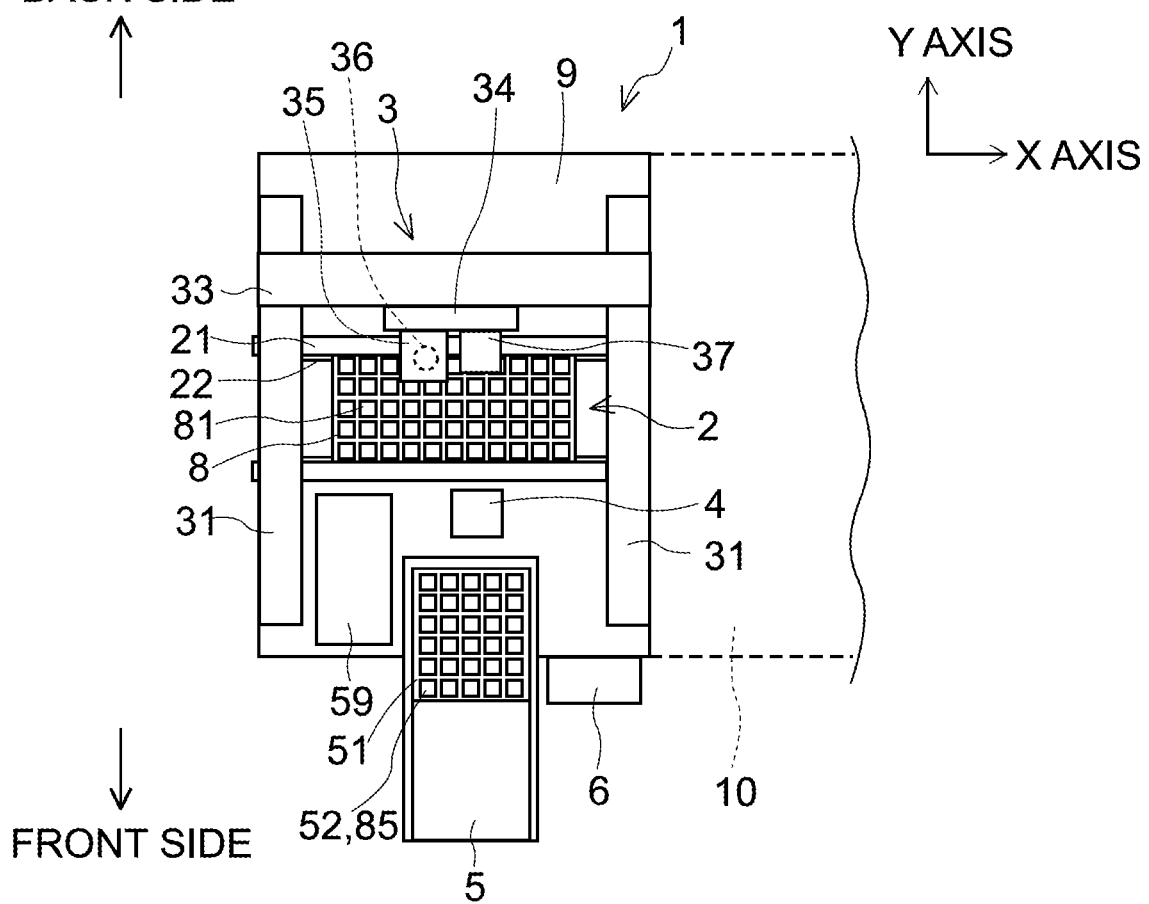
FIG. 1 is a plan view schematically illustrating a configuration of a board inspection machine of a first embodiment of the present disclosure.

A configuration of a board inspection machine 1 of a first embodiment of the present disclosure will be described with reference to FIG. 1. FIG. 1 is a plan view schematically illustrating a configuration of the board inspection machine of the first embodiment of the present disclosure. A direction from the left side to the right side in FIG. 1 is an X-axis direction through which a carrier member 8 is conveyed. The lower side in FIG. 1 is the front side of the board inspection machine 1, the upper side thereof is the back side, and a direction from the front side to the back side is a Y-axis direction. The board inspection machine 1 is disposed in an upstream process of the solder printing machine 10, and sets an individual board 85, as an inspection target, before solder paste is printed. The board inspection machine 1 is configured by assembling a carrier conveyance device 2, a board lifting-up device 3, a three-dimensional coplanarity inspection device 4, the board supplying device 5, a control device 6, and the like on a device table 9.

Figure 2:
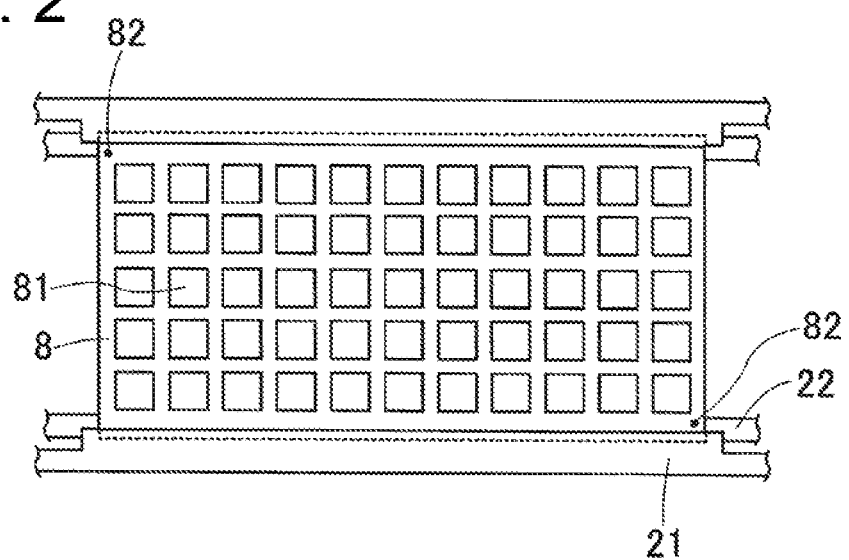
FIG. 2 is a plan view of a carrier member positioned at a working position.

The carrier conveyance device 2 loads the carrier member 8, positions it at a working position approximately at the center of the device table 9, and unloads it to the solder printing machine 10. FIG. 2 is a plan view of the carrier member 8 positioned at the working position. The carrier member 8 is formed in a rectangular plate shape by using a resin or the like. The carrier member 8 has multiple concave cavity sections 81 having a shallow bottom, and accommodates one individual board 85 in each cavity section 81. In FIG. 2, the approximately square cavity sections 81 are arranged in a two-dimensional lattice pattern of 5 rows and 11 columns. A position fiducial mark 82 is attached to each of two corners positioned on a diagonal line of the carrier member 8.

The carrier conveyance device 2 is configured with a backup device (not shown in FIG. 1) and the like such as a pair of guide rails 21 and a pair of conveyor belts 22. The pair of guide rails 21 extend in a conveyance direction (X-axis direction) across the center of an upper face of the device table 9, and is assembled on the device table 9 in parallel to each other. The pair of endless annular conveyor belts 22 are arranged on an inner side of the pair of guide rails 21 facing each other. The pair of conveyor belts 22 rotate in a state where edges of two opposite sides of the carrier member 8 are placed on a conveyor conveyance surface, and performs loading and unloading. The backup device is disposed below the working position. The backup device pushes up the carrier member 8 to clamp it in a horizontal posture and positions it.

The board lifting-up device 3 is an XY-robot type device which can be horizontally moved in an X-axis direction and a Y-axis direction. The board lifting-up device 3 not only lifts up the individual board 85 but also transfers it. The board lifting-up device 3 is configured with a pair of Y-axis rails 31 and a Y-axis slider 33, a work head 34, a nozzle tool 35, a suction nozzle 36, a position detecting camera 37, and the like configuring a head driving mechanism. The pair of Y-axis rails 31 are arranged near both side faces of the device table 9, and extends in a front-rear direction (Y-axis direction). The Y-axis slider 33 is movably mounted on the pair of Y-axis rails 31. The Y-axis slider 33 is driven in the Y-axis direction by a Y-axis ball screw mechanism (not shown).

The work head 34 is movably mounted on the Y-axis slider 33. The work head 34 is driven in the X-axis direction an X-axis ball screw mechanism (not shown). The nozzle tool 35 is exchangeably held at the work head 34. The nozzle tool 35 includes the suction nozzle 36 on a lower side. The suction nozzle 36 sucks and lifts up an upper face of the individual board 85 by using negative pressure. The present disclosure is not limited thereto, and the nozzle tool 35 may have a clamping chuck that nips and lifts up the individual board 85. The position detecting camera 37 is disposed on the work head 34 by being implemented in parallel with the nozzle tool 35. The position detecting camera 37 images the position fiducial mark 82 attached to the carrier member 8 and detects an accurate position of the carrier member 8.

The three-dimensional coplanarity inspection device 4 (hereafter, it is abbreviated as inspection device 4) is provided on an upper face of the device table 9 of the front side of the carrier conveyance device 2. The inspection device 4 is disposed upward and inspects a lower surface of the individual board 85 from below. The inspection device 4 is an embodiment of a flatness inspection device of the present disclosure which determines whether or not to use it by inspecting flatness of the lifted individual board 85. The flatness inspection device is not limited to the three-dimensional coplanarity inspection device 4, but may be a scan type flatness inspection device which horizontally moves the individual board 85 at a position above a height detecting section and detects the height of each section of the individual board 85.

The board supplying device 5 is provided on an upper face of the device table 9 of the front side of the inspection device 4. The board supplying device 5 includes a pallet conveyance mechanism (not shown) that loads and unloads a tray 51 on which multiple individual boards 85 are placed and a pallet on which the tray 51 is placed. The tray 51 includes multiple cavity sections 52 for accommodating the individual boards 85 one by one. Multiple trays 51 are stacked and placed on the pallet. The upper tray 51 is collected when whole individual boards 85 are used and become empty. With this, the lower tray 51 accommodating the individual board 85 in each cavity section 52 can be used.

A collection tray 59 is disposed on an upper face of the device table 9 near the inspection device 4 and the board supplying device 5. The collection tray 59 on which the individual board 85 determined to be unusable by the inspection device 4 is placed is collected by an operator.

The control device 6 is assembled to the device table 9, and its installation position is not particularly limited. The control device 6 controls an operation of the carrier conveyance device 2, the board lifting-up device 3, the inspection device 4, and the board supplying device 5. The control device 6 includes a display section that displays information to an operator, an input section that can input setting by the operator, and a communication section that exchanges information with other control devices. A control function of the control device 6 will be described together with an operation of the board inspection machine 1.

(2. Operation of Board Inspection Machine 1 of First Embodiment)

Figure 3:
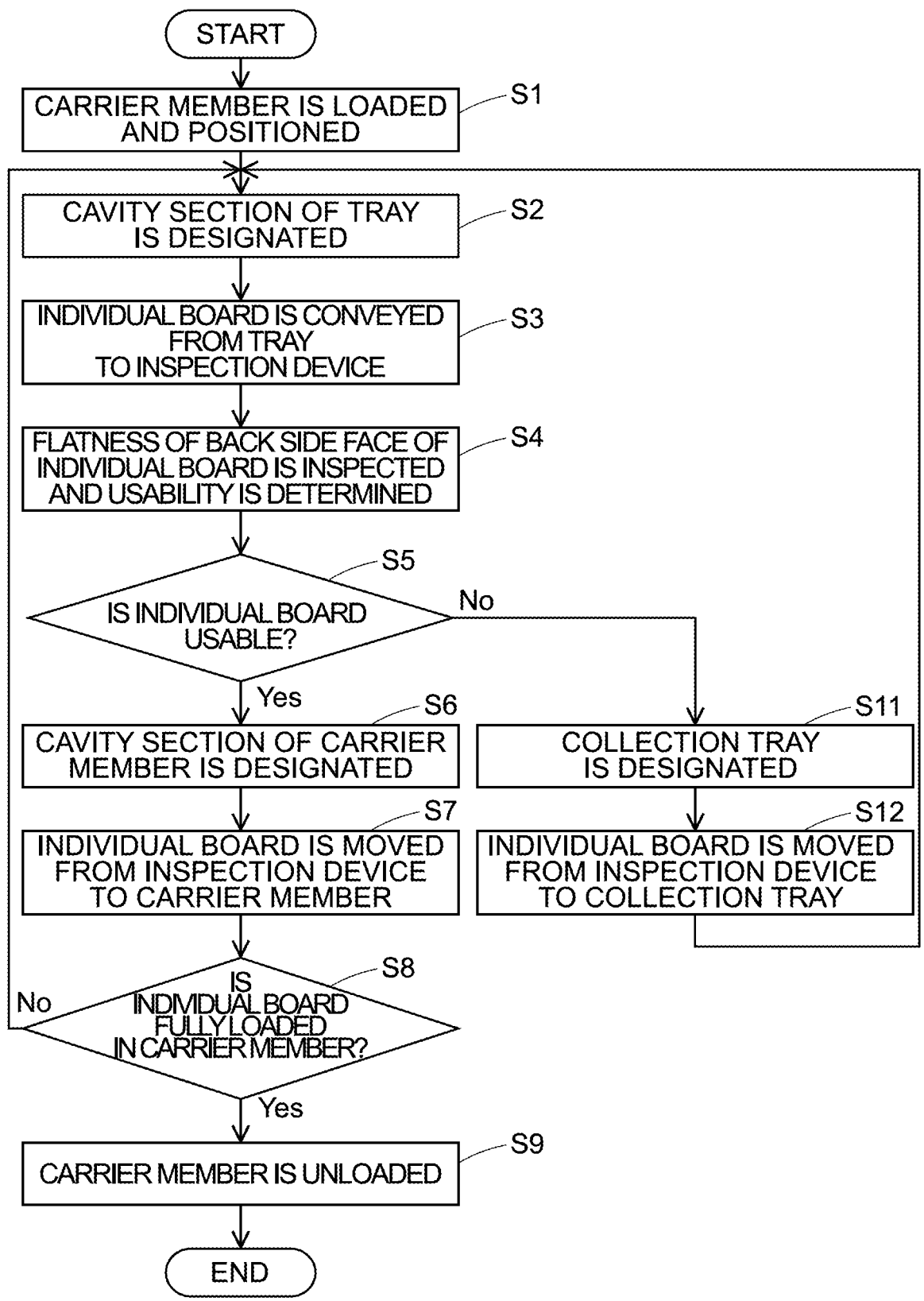
FIG. 3 is an operation flow diagram of a board inspection machine of the first embodiment.
Figure 4:
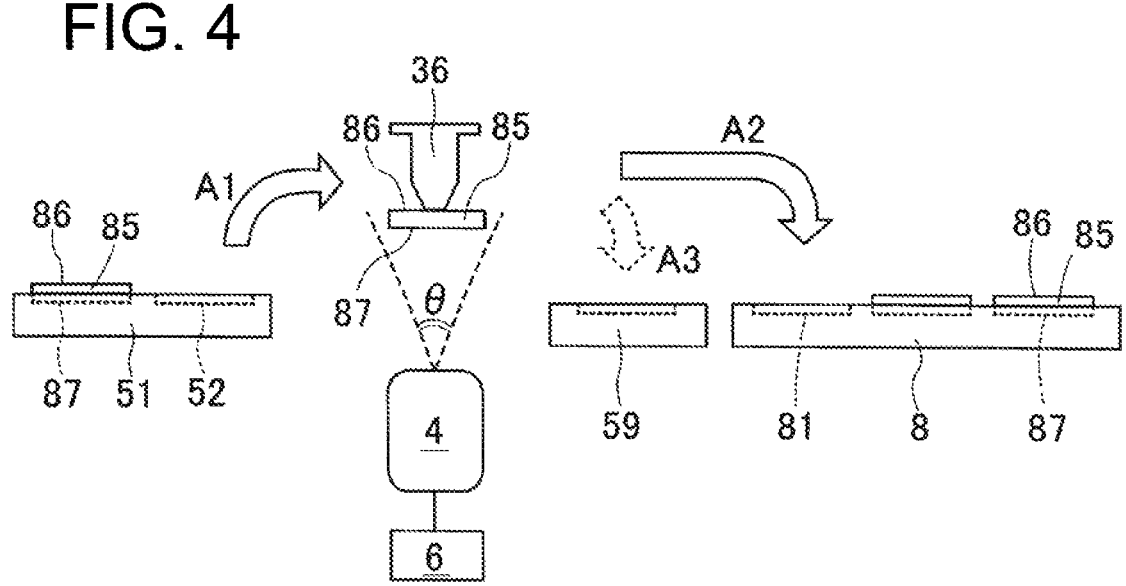
FIG. 4 is a side view for schematically explaining an operation of the board inspection machine of the first embodiment.

In the board inspection machine 1 of the first embodiment, an empty carrier member 8 is loaded by the carrier conveyance device 2, and the individual board 85 is moved from the tray 51 to the carrier member 8 by the board lifting-up device 3. The inspection device 4 inspects the flatness of the individual board 85 during moving and lifted by the board lifting-up device 3 from below. FIG. 3 is an operation flow diagram of the board inspection machine 1 of the first embodiment. In addition, FIG. 4 is a side view schematically explaining an operation of the board inspection machine 1 of the first embodiment. The operation of the board inspection machine 1 is mainly progressed by a control function the control device 6.

In an initial state, it is assumed that the multiple trays 51 on which the individual boards 85 are stacked are loaded on the board supplying device 5 in advance. In step S1 of FIG. 3, in accordance with an instruction from the control device 6, the carrier conveyance device 2 loads the empty carrier member 8 and positions it at the working position. In next step S2, the control device 6 designates the tray 51 or the cavity section 52 and instructs the designated result to the board lifting-up device 3. In step S3, the board lifting-up device 3 moves the suction nozzle 36 above the designated cavity section 52, and sucks and lifts up the individual board 85 from the cavity section 52. Next, the board lifting-up device 3 transfers the individual board 85 by moving the suction nozzle 36 above the inspection device 4. An operation of the board lifting-up device 3 in step S3 is illustrated by an arrow A1 in FIG. 4.

In step S4, the inspection device 4 inspects the flatness of the individual board 85 and determines whether or not it can be used in accordance with an instruction from the control device 6. More specifically, the inspection device 4 is the three-dimensional coplanarity inspection device 4 that performs imaging at an upward imaging view angle θ illustrated in FIG. 4. Then, within a range of the imaging view angle θ, the whole individual boards 85 lifted by the suction nozzle 36 are contained. The inspection device 4 images a back side face 87 of the individual board 85 by one image, and inspects the coplanarities of multiple predetermined positions of the individual boards 85.

That is, the inspection device 4 performs image analysis with respect to a captured image, and inspects whether or not multiple predetermined positions of the individual boards 85 are approximately within one plane. The inspection device 4 determines that the individual board 85 is usable when the flatness is good that the multiple positions are within one plane, and determines that the individual board 85 is unusable when the flatness is not good. The inspection device 4 transfers an inspection determination result to the control device 6.

In step S5, if the inspection determination result is usable, an operation flow of the control device 6 proceeds to step S6, and if the inspection determination result is unusable, the operation flow of the control device 6 proceeds to step S11. In step S6, the control device 6 designates the carrier member 8 or the cavity section 81, and instructs the designated result to the board lifting-up device 3. In step S7, the board lifting-up device 3 moves the suction nozzle 36 from above of the inspection device 4 to above of the designated cavity section 81, and places the individual board 85 on the designated cavity section 81. An operation of the board lifting-up device 3 of step S7 is illustrated by an arrow A2 of FIG. 4. The movement of one individual board 85 is completed by a series of operations from step S2 to step S7.

In step S8, the control device 6 determines whether or not it is in a fully loaded state in which the individual boards 85 are placed in whole cavity sections 81 of the carrier member 8. When it is not in the fully loaded state, the operation flow of the control device 6 returns to step S2, and starts the movement of the next individual board 85. By repeating the series of the operations from step S2 to step S8, positions of the cavity sections 52 of the tray 51 and positions of the cavity sections 81 of the carrier member 8 are sequentially changed and designated. When the movement of the individual board 85 to the cavity sections 81 that are arranged in 5 rows and 11 columns is performed 55 times, the carrier member 8 is in the fully loaded state where the individual boards 85 are accommodated in whole cavity sections 81. Then, the operation flow of the control device 6 proceeds from step S8 to step S9, and exits an iteration loop. In step S9, the carrier conveyance device 2 unloads the carrier member 8 of the fully loaded state in the solder printing machine 10.

In addition, the control device 6 designates the collection tray 59, and instructs the designated result to the board lifting-up device 3 in step S11 which is advanced when the inspection determination result in step S5 is unusable. In step S12, the board lifting-up device 3 moves the suction nozzle 36 from above of the inspection device 4 to above of the collection tray 59, and places the unusable individual board 85 on the collection tray 59. An operation of the board lifting-up device 3 of step S12 is illustrated by a dashed arrow A3 of FIG. 4. Then, the operation flow of the control device 6 returns to step S2, and the movement of the next individual board 85 starts. The unusable individual board 85 collected by the collection tray 59 is repaired and provided to be used, and discarded when it is hard to repair.

(3. Aspect and Effect of First Embodiment of Board Inspection Machine 1)

The board inspection machine 1 of the first embodiment includes the carrier conveyance device 2 that loads, positions, and unloads the carrier member 8 on which multiple the individual boards 85 on which components are mounted by printing solder paste are placed, the board lifting-up device that lifts up the individual board 85, and the three-dimensional coplanarity inspection device 4 (flatness inspection device) that inspects the flatness of the lifted individual board 85 and determines whether or not usability the individual board 85.

According to this, since the multiple individual boards 85 are sequentially lifted by the board lifting-up device 3 and the flatness can be sequentially inspected by the inspection device 4, efficient inspection is performed. In addition, since the full inspection is performed with respect to the flatness of the multiple individual boards 85, the quality of the individual board 85 is improved.

Furthermore, the board inspection machine 1 of the first embodiment further includes the board supplying device 5 that moves the individual board 85 on the tray 51 and supplies the individual board 85, the board lifting-up device 3 places the individual board 85 lifted from the tray 51 on the carrier member 8 positioned through the inspection device 4, and the inspection device 4 inspects the flatness of the individual board 85 during moving. According to this, since inspection of the flatness required in the related art is performed during a movement operation for the individual board 85, an inspection time is efficient without prolonging.

Furthermore, the board lifting-up device 3 moves only the individual board 85 determined to be used by the inspection device 4 on the carrier member 8. According to this, the individual board 85 determined to be unusable is not placed on the carrier member 8, and not conveyed to a downstream side process. Meanwhile, in the related art, when the individual board 85 is moved from the tray 51 to the carrier member 8, the inspection of the flatness is not performed. Alternatively, after components are mounted by conveyance the whole individual boards 85 to the downstream side process, inspection of a mounting state of the component and the inspection of the flatness of the individual board 85 are performed at the same time. Therefore, if the flatness of the individual board 85 is not good, waste of components and the individual board 85 occurs. However, in the first embodiment, since the individual board 85 determined to be unusable is collected and repaired, the waste of components and the individual board 85 does not occur.

Furthermore, the flatness inspection device is the three-dimensional coplanarity inspection device 4 which inspects the coplanarity of multiple predetermined positions of the individual boards 85 by imaging the back side face 87 of the individual board 85 as one image. According to this, since it is a method in which the image analysis is performed after one image is captured, it is more efficient than a scan type flatness inspection device or the like in that it is performed during a short inspection time.

(4. Configuration of Board Inspection Machine 1A of Second Embodiment)

Figure 5:
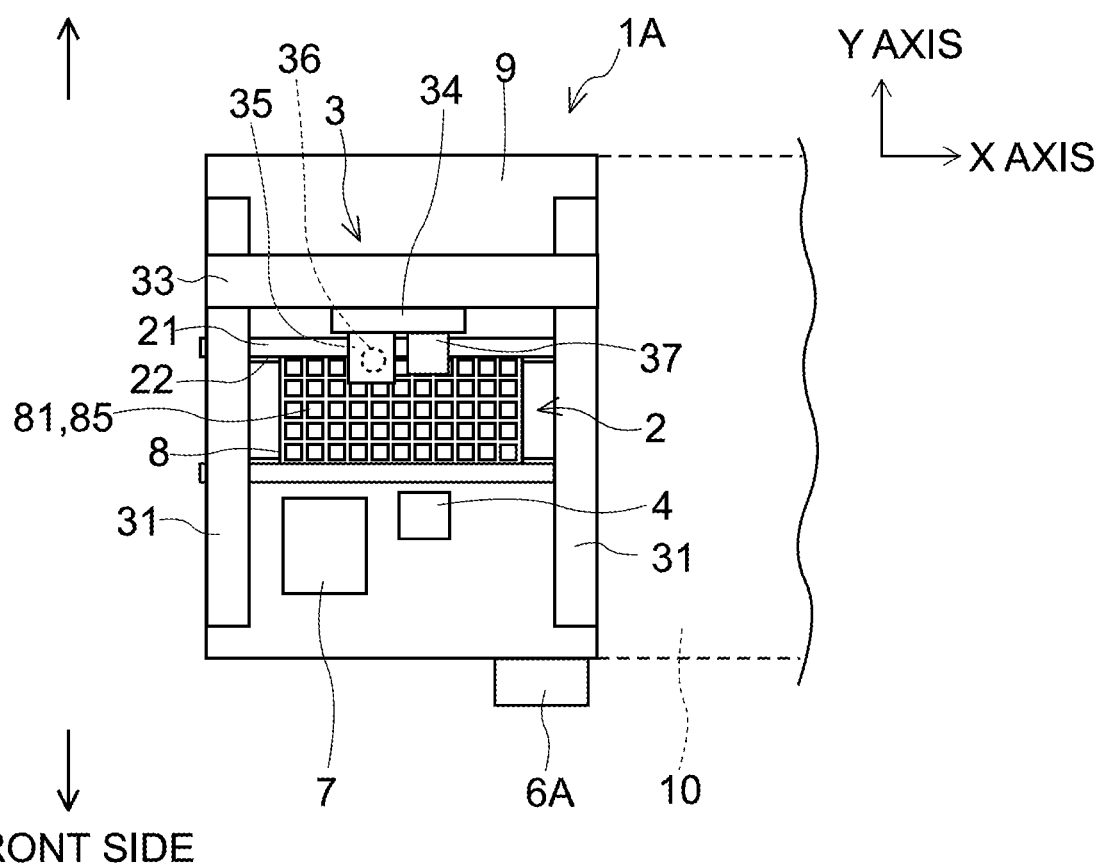
FIG. 5 is a plan view schematically illustrating a configuration of a board inspection machine of a second embodiment.

Next, for a board inspection machine 1A of a second embodiment, points different from the first embodiment will be mainly described. FIG. 5 is a plan view schematically illustrating a configuration of the board inspection machine 1A of the second embodiment. The board inspection machine 1A of the second embodiment includes a board inverting section 7 without including the board supplying device 5 and the collection tray 59. The board inverting section 7 is disposed on the upper face of the device table 9 near the carrier conveyance device 2 and the three-dimensional coplanarity inspection device 4. The board inverting section 7 inverts the front side face 86 and the back side face 87 of the individual board 85 such that the front side face 86 of the individual board 85 is inspected. The board inverting section 7 can be configured by appropriately applying a known technology. In addition, a control device 6A of the second embodiment has a control function different from that of the control device 6 of the first embodiment.

(5. Operation of Board Inspection Machine 1A of Second Embodiment)

Figure 6:
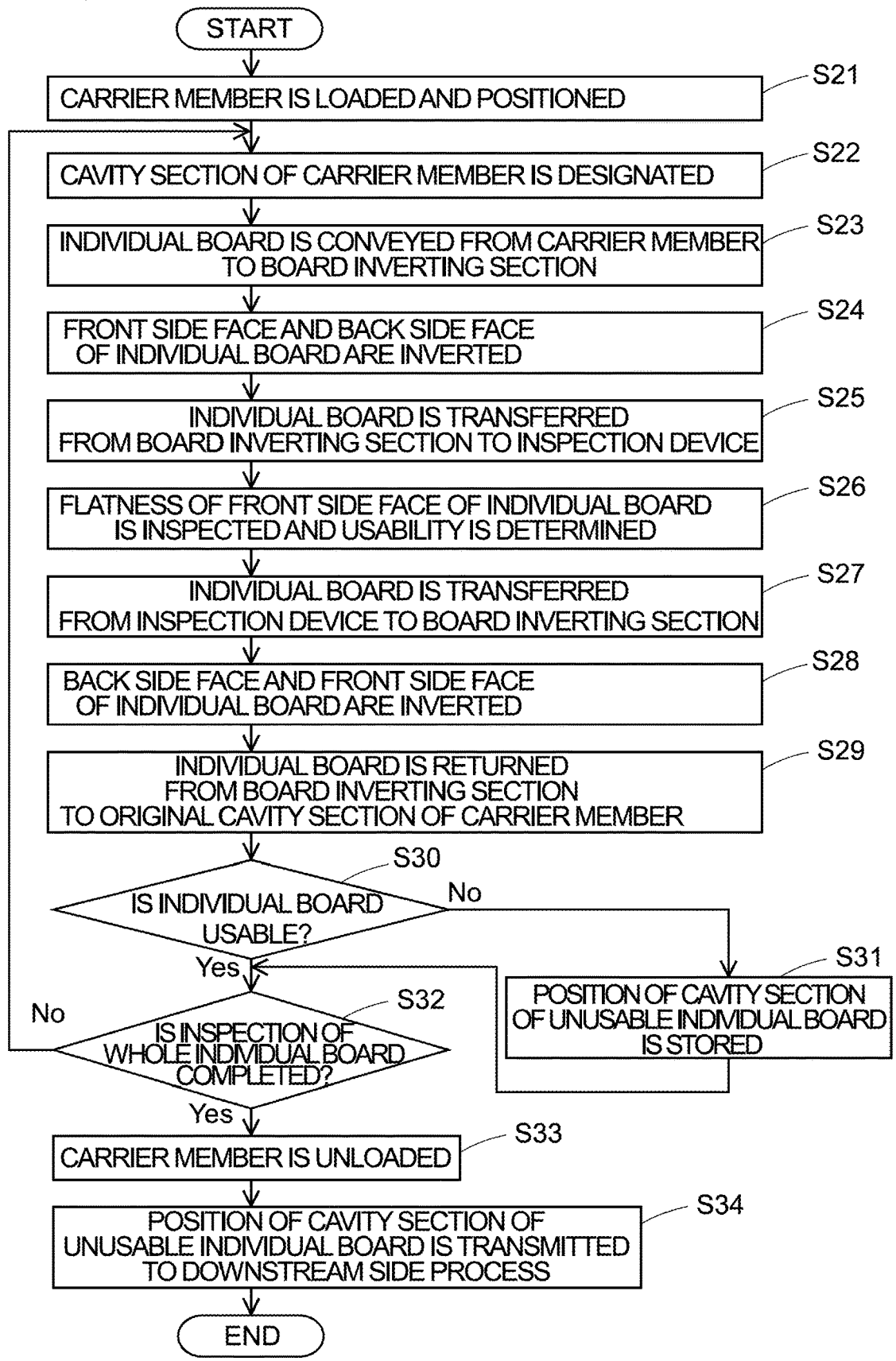
FIG. 6 is an operation flow diagram of the board inspection machine of the second embodiment.
Figure 7:
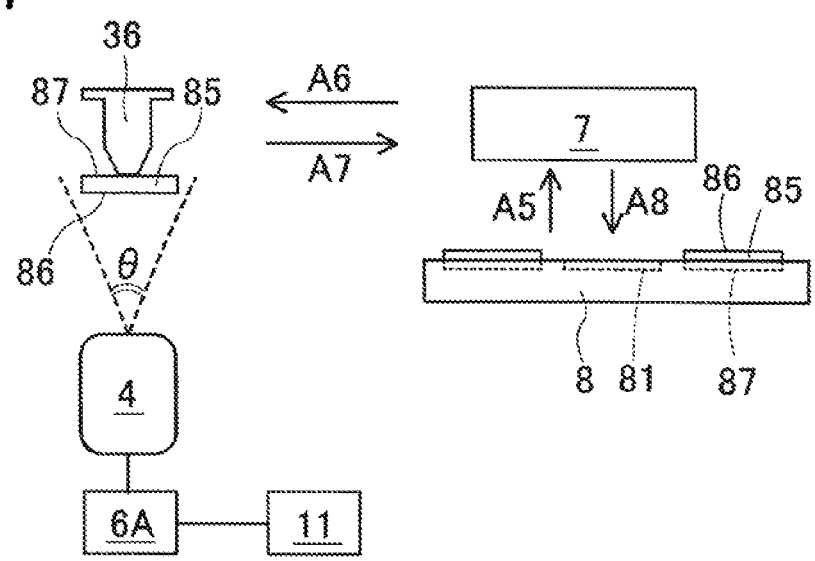
FIG. 7 is a side view for schematically explaining an operation of the board inspection machine of the second embodiment.

In the board inspection machine 1A of the second embodiment, the carrier conveyance device 2 loads the carrier member 8 on which the individual boards 85 are fully loaded. The board lifting-up device 3 transfers and returns the individual board 85 through the board inverting section 7 between the carrier member 8 and the inspection device 4. FIG. 6 is an operation flow diagram of the board inspection machine 1A of the second embodiment. In addition, FIG. 7 is a side view schematically explaining an operation of the board inspection machine 1A of the second embodiment. An operation of the board inspection machine 1A proceeds mainly by a control function of the control device 6A.

In step S21 of FIG. 6, the carrier conveyance device 2 loads the carrier member 8 of the fully loaded state on which respective individual boards 85 are accommodated in the cavity sections 81 in accordance with an instruction from the control device 6A, and positions the carrier member 8 on the working position. In step S22, the control device 6A designates a certain cavity section 81 of the carrier member 8, and instructs the designated result to the board lifting-up device 3. In step S23, the board lifting-up device 3 moves the suction nozzle 36 above of the designated cavity sections 81, and absorbs and lifts up the individual board 85 from the designated cavity sections 81. Next, the board lifting-up device 3 moves the suction nozzle 36 to the board inverting section 7, and places the individual board 85 in the board inverting section 7 (see arrow A5 of FIG. 7).

In step S24, the board inverting section 7 inverts the front side face 86 and the back side face 87 of the individual board 85. In step S25, the board lifting-up device 3 sucks and lifts up the individual board 85 from the board inverting section 7, and moves the suction nozzle 36 above the inspection device 4 (see arrow A6 FIG. 7). In step S26, in accordance with an instruction from the control device 6A, the inspection device 4 inspects the flatness of the front side face 86 under the individual board 85 and determines whether or not to use it. With this, since the front side face 86 on which components are actually mounted can be inspected, a detection accuracy of the flatness is improved. Furthermore, it is preferable to set pad portions for soldering component terminals as multiple places of the individual boards 85 of which the flatness is inspected. According to this, the detection accuracy of the flatness is further improved. The inspection device 4 transmits the inspection determination result to the control device 6A.

In step S27, the board lifting-up device 3 moves the suction nozzle 36 to the board inverting section 7, and places the individual board 85 on which the inspection is completed on the board inverting section 7 (see arrow A7 of FIG. 7). In step S28, the board inverting section 7 inverts the back side face 87 and the front side face 86 of the individual board 85. In step S29, the board lifting-up device 3 moves the suction nozzle 36 above the designated original cavity section 81 by sucking and lifting up the individual board 85 from the board inverting section 7. Next, the board lifting-up device 3 places the individual board 85 on the original cavity section 81 in a posture positioned on the front side face 86 by returning the individual board 85 (see arrow A8 of FIG. 7).

In step S30, if the inspection determination result is usable, the operation flow of the control device 6 proceeds to step S32, and if the inspection determination result is unusable, the operation flow proceeds to step S31. In step S31, the control device 6 stores the position of the cavity section 81 in which the individual board 85 determined to be unusable is accommodated, and causes the operation flow to be merged with step S32. At the series of the operations from step S22 to step S31, the inspection on one individual board 85 is completed.

In step S32, the control device 6 determines whether or not the inspection on the whole individual boards 85 above the carrier member 8 is completed. When it is not completed, the operation flow of the control device 6 returns to step S22, and the inspection on the next individual board 85 starts. By repeating the series of the operations from step S22 to step S32, the positions of the cavity sections 81 of the carrier member 8 are sequentially changed and designated. The inspection on the whole individual boards 85 of the cavity sections 81 that are arranged in 5 rows and 11 columns is completed at 55 times, Then, the operation flow of the control device 6 proceeds from step S32 to step S33, and exits from the iteration loop.

In step S33, the carrier conveyance device 2 unloads the carrier member 8 to the solder printing machine 10. In the next step S34, the control device 6 transmits the position of the cavity section 81 stored in step S31 to a downstream side process. In other words, the control device 6 transmits the position of the cavity section 81 in which the individual board 85 determined to be unusable is accommodated to the downstream side process. There are cases where there are multiple positions of corresponding cavity sections 81, and there are cases where there are none.

In the second embodiment, a destination address of the position of the cavity section 81 is set to a control section of a component mounting machine 11 in a downstream side of the solder printing machine 10. A transmission route is not limited to a direct route from the control device 6 to the component mounting machine 11, and may be an indirect route through the solder printing machine 10 or through a higher host computer. A control function in step S34 of the control device 6A corresponds to a position transmitting section of the present disclosure.

Then, in the solder printing machine 10 of the downstream side, solder paste is printed on whole individual boards 85 irrespective of usability. Furthermore, in the component mounting machine 11 of the downstream side, a component is mounted on only the individual board 85 determined to be usable. In the second embodiment, the individual board 85 different from the first embodiment determined to be unusable is not collected. For this reason, when the individual board 85 is collected, solder printing is performed in a state where the cavity sections 81 of apart of the carrier member 8 are empty such that the flatness of a screen used in the printing becomes unstable, and the solder is additionally leaked to the empty cavity section 81.

(6. Aspect and Effect of Board Inspection Machine 1A of Second Embodiment)

In the board inspection machine 1A of the second embodiment, the carrier conveyance device 2 loads and positions the carrier member 8 on which the multiple the individual boards 85 are placed, and the board lifting-up device 3 lifts up the individual board 85 from the positioned carrier member 8, transports the lifted individual board 85 to the three-dimensional coplanarity inspection device 4 (flatness inspection device), and returns the individual board 85 to the original position on the carrier member 8 when the inspection is completed by the inspection device 4. According to this, even in a configuration in which the individual boards 85 are placed on the carrier member 8 from the beginning, since the flatness can be sequentially inspected, efficient inspection is performed. In addition, since the full inspection is performed with respect to the flatness of the multiple individual boards 85, the quality of the individual board 85 is improved.

Furthermore, the board inspection machine 1A of the second embodiment further includes the position transmitting section (control function in step S34 of control device 6A) that transmits the position of the individual board 85 determined to be unusable by the inspection device 4 above the carrier member 8 to the downstream side process. According to this, in the component mounting machine 11 of the downstream side, since a component can be mounted on only the individual board 85 determined to be usable, waste of the component does not occur.

Furthermore, the inspection device 4 performs the inspection below the individual board 85 and further includes the board inverting section 7 that inverts the front side face 86 and the back side face 87 of the individual board 85 so that the front side face 86 of the individual board 85 is inspected. According to this, since the flatness of the front side face 86 for mounting a component on the individual board 85 is inspected, the detection accuracy of the flatness is improved more than the flatness required for the inspection of the back side face 87 and a determination accuracy of the usability is also improved.

The board inverting section 7 used in the second embodiment can also be incorporated in the board inspection machine 1 of the first embodiment. In this case, in step S3, the individual board 85 passes through the board inverting section 7 during the individual board 85 is moved from the tray 51 to the inspection device 4, and in step S7, the individual board 85 passes through the board inverting section 7 during the individual board 85 is transferred from the inspection device 4 to the carrier member 8. Various applications and modifications can also be applied to the present disclosure.

REFERENCE SIGNS LIST

1, 1A: board inspection machine, 2: carrier conveyance device, 3: board lifting-up device, 36: suction nozzle, 4: three-dimensional coplanarity inspection device (flatness inspection device), 5: board supplying device, 51: tray, 52: cavity section, 59: collection tray, 6, 6A: control device, 7: board inverting section, 8: carrier member, 81: cavity section, 85: individual board, 86: front side face, 87: back side face, 9: device table, 10: solder printing machine, 11: component mounting machine

The invention claimed is:

1. A board inspection machine comprising:
a carrier conveyance device that loads, positions, and unloads a carrier member on which multiple individual boards are placed, solder paste being printed and a component being mounted on an upper surface of the individual boards;
a suction nozzle that picks up the component
a board lifting-up device including the suction nozzle, the board lifting-up device lifting up the individual board provided in a cavity section of the carrier member from the upper surface of the individual board using the suction nozzle; and
a flatness inspection device that inspects flatness of a lower surface of the lifted individual board and determines usability of the individual board by performing imaging at an upward imaging view angle and inspecting coplanarities at predetermined positions of the lifted individual board.

2. The board inspection machine of claim 1, further comprising:
a board supplying device that moves the individual board on a tray and supplies the moved individual board,
wherein the board lifting-up device lifts up the individual board from the tray and transfers the lifted individual board on the positioned carrier member through the flatness inspection device, and
the flatness inspection device inspects the flatness of the individual board during transfer.

3. The board inspection machine of claim 2,
wherein the board lifting-up device moves only the individual board determined to be usable by the flatness inspection device on the carrier member.

4. The board inspection machine of claim 1,
wherein the carrier conveyance device loads and positions the carrier member on which multiple individual boards are placed, and
the board lifting-up device lifts up the individual board from the positioned carrier member and transports the individual board to the flatness inspection device, and returns the individual board to an original position on the carrier member when inspection is completed by the flatness inspection device.

5. The board inspection machine of claim 4, further comprising:
a control device configured to transmit a position on the carrier member of the individual board determined to be unusable in the flatness inspection device, to a downstream side process.

6. The board inspection machine of claim 1,
wherein the flatness inspection device includes a board inverting section that inverts a front side face and a back side face of the individual board such that the front side face of the individual board is inspected.

7. The board inspection machine of claim 6,
wherein the flatness inspection device is a three-dimensional coplanarity inspection device which inspects coplanarity by imaging the front side face or back side face of the individual board as one image.

8. The board inspection machine of claim 1,
wherein the board inspection machine is disposed in an upstream process of a solder printing machine in which the solder paste is printed on the individual board.

9. A board inspection machine comprising:
a carrier conveyance device that loads, positions, and unloads a carrier member on which multiple individual boards are placed, solder paste being printed and a component being mounted on an upper surface of the individual boards;
a board lifting-up device that sequentially lifts up the individual board from the upper surface of the individual board provided in a cavity section of the carrier member before the component is mounted on the upper surface of the individual board and the solder paste is printed; and a flatness inspection device that sequentially inspects flatness of a lower surface of the lifted individual board and determines usability of the individual board.

\* \* \* \* \*